(12) United States Patent
Want et al.

(10) Patent No.: US 6,210,383 B1
(45) Date of Patent: Apr. 3, 2001

(54) FLUID RECOVERY SYSTEM

(75) Inventors: Nicholas Want, Manchester; Theodore Karwoski, Hollis; Steve A. Herweck; Ralph L. Gillis, both of Nashua; Craig J. Weimer, Hollis, all of NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/240,127

(22) Filed: Jan. 29, 1999

(51) Int. Cl.⁷ .................................................. A61M 1/00
(52) U.S. Cl. ............................................................ 604/318
(58) Field of Search .................... 604/4.01, 317, 604/319, 322, 403, 404, 409, 410, 133, 141, 318

(56) References Cited

U.S. PATENT DOCUMENTS

| | | | |
|---|---|---|---|
| Re. 35,225 | 4/1996 | Herweck et al. | 604/321 |
| D. 328,790 | 8/1992 | Herweck et al. | D24/169 |
| D. 340,285 | 10/1993 | Herweck et al. | D24/169 |
| 3,363,626 | 1/1968 | Bidwell et al. | . |
| 4,258,824 | 3/1981 | Kurtz et al. | 181/233 |
| 4,544,370 | 10/1985 | Elliott et al. | 604/319 |
| 4,550,749 | 11/1985 | Kirkorian | 137/843 |
| 4,605,400 | 8/1986 | Kurtz et al. | 604/319 |
| 4,715,856 | 12/1987 | Elliott et al. | 604/321 |
| 4,738,671 | 4/1988 | Elliott et al. | 604/319 |
| 4,747,844 | 5/1988 | Elliott | 604/319 |
| 4,988,342 | 1/1991 | Herweck et al. | 604/321 |
| 5,114,416 | 5/1992 | Karwoski et al. | 604/321 |
| 5,141,504 | 8/1992 | Herweck et al. | 604/317 |
| 5,154,712 | 10/1992 | Herweck et al. | 604/321 |
| 5,286,262 | 2/1994 | Herweck et al. | 604/321 |
| 5,300,050 | 4/1994 | Everett et al. | 604/320 |
| 5,380,314 | 1/1995 | Herweck et al. | 604/403 |
| 5,397,299 | 3/1995 | Karwoski et al.. | 604/4 |
| 5,401,262 | * 3/1995 | Karwoski et al. | 604/321 |
| 5,507,734 | 4/1996 | Everett et al. | 604/318 |
| 5,722,964 | 3/1998 | Herweck et al. | 604/317 |
| 5,807,358 | 9/1998 | Herweck et al. | 604/320 |
| 5,865,408 | 2/1999 | Swisher et al. | 248/188.12 |

FOREIGN PATENT DOCUMENTS

WO 98/30256   7/1998   (WO) .

* cited by examiner

*Primary Examiner*—Anh-Tuan T. Nguyen
(74) *Attorney, Agent, or Firm*—Lahive & Cockfield, LLP

(57) ABSTRACT

A fluid recovery system, such as a chest or thoracic cavity drain, having a collection chamber for collecting fluid from a patient includes a base and a front face having a translucent portion for viewing the collected fluid and monitoring operation of the system. The front face is coupled to the base at an acute angle to facilitate viewing of the collected fluid, and measurement of the fluid volume, from a position substantially above the fluid recovery system. Additionally, a column insert can be positioned within the collection chamber to collect an initial volume of the fluid and to allow precise determination of its volume.

10 Claims, 10 Drawing Sheets

FLUID RECOVERY SYSTEM

BACKGROUND OF THE INVENTION

The present invention relates to apparatuses for draining fluid from a patient, and more particularly, to fluid recovery systems for draining blood from the thoracic cavity of the patient.

Various devices have been developed to drain and collect fluids such as blood from the body cavity of a patient. Such devices typically employ a vacuum to the body cavity of the patient sufficient enough to maintain high "siphon" potential for the removal of blood or other fluid following trauma or surgery. One example of such a draining device is a chest drain, also known as a thoracic cavity drain. Generally, a chest drain is a relatively compact bedside vessel employed to collect fluids postoperatively from a closed surgical site, for example, through a drain tube implanted in the patient's chest.

In many medical situations in which fluids are drawn from a patient, it is critical to accurately measure and monitor the initial volume, for example the first 100, of fluid collected from the patient. Conventional fluid recovery systems generally include a collection chamber having a cut-away portion that provides a section of reduced volume within the collection chamber for receiving the initial volume of fluid collected from the patient. The reduced volume section of the collection chamber permits more accurate monitoring and measuring of the initial fluid collected as changes in the fluid volume collected within the reduced volume section can be measured in smaller increments and at higher resolution.

However, provision of the reduced volume section within the collection chamber has a number of disadvantages. For example, providing a cut-away portion in the collection chamber reduces the total volume of the collection chamber and results in the collection chamber having a non-uniform cross-section, which can complicate manufacturing of the chest drain and can increase production costs. This is particularly true if the fluid recovery system is manufactured through an injection molding process, as a complicated mold must be constructed to produce the reduced volume section of the collection chamber. Moreover, provision of the cut-away portion of the collection chamber can reduce the stability of the fluid recovery system, rendering the chest drain susceptible knock-over, which can adversely effect the operation of the chest drain.

In a hospital setting, a fluid recovery system is typically positioned on the floor further increasing the difficulty in monitoring the volume of fluid collected within the collection chamber of the system. Often, medical personnel must either lift the entire system to bring the system to eye-level or bend-over to accurately measure the fluid volume within the system and monitor the operation of the system. Moreover, glare from overhead lights on the translucent face of the collection chamber can interfere with accurate and reliable monitoring of the fluid volume within the collection chamber.

Accordingly, there is a need for a fluid recovery system that provides for reliable and accurate monitoring of the fluid collected from the patient, particularly the initial volume of fluid collected from the patient.

SUMMARY OF THE INVENTION

The present invention provides a fluid recovery system for collecting fluid from a patient that provides for reliable and accurate monitoring of the operation of the fluid recovery system, in particular the volume of fluid recovered from the patient, under a wide range of operating conditions.

A fluid recovery system of the present invention includes a housing having a base and a collection chamber therein for collecting a volume of fluid from a patient. The fluid recovery system further includes a front face coupled to the housing, at least a portion of which is translucent, preferably transparent, to allow monitoring of the operation of the system, in particular to permit measuring of the fluid collected within the collection chamber. The front face is preferably positioned at an acute angle relative to the base of the housing to facilitate monitoring of the operation of the fluid recovery system through the translucent front face. In particular, the acutely angled front face allows a medical professional to view and to accurately measure the collected fluid volume with ease from a position substantially above the fluid recovery system. For example, the acutely angled front face permits a medical professional to measure the volume of collected fluid within a fluid recovery system positioned on the floor from a standing position, without having to compensate for measurement discrepancies due to the height difference between the standing medical professional and the fluid recovery system positioned on the floor.

According to one aspect of the invention, the acute angle of the front face can be less than or equal to 85°, and preferably is substantially equal to 75°. Such an acute angle between the base and the face of the fluid recovery system allows viewing of the translucent portion of the front face from a position substantially above the fluid system such that the line of sight intersecting the translucent portion of the front face forms a substantially normal angle with the front face.

According to another aspect of the invention, a graduated scale, typically in the form of spaced-apart fluid volume markings, provided on the front face of the housing for measuring the volume of the fluid collected within the collection chamber is configured to compensate for the acutely angled front face. In particular, the volume markings of the graduated scale are spaced to compensate for the particular acute angle of the front face relative to the base of the housing. For example, as the fluid is collected within the collection chamber, the height of the fluid within the collection chamber increases. The acute angle of the front face can result in a non-linear relationship between an incremental rise in the height of the fluid and the corresponding incremental increase in its volume. The graduated scale is preferably configured to compensate for such a non-linearity.

According to another aspect of the invention, the fluid recovery system includes a top surface, a rear surface, and two side surfaces. The front face extends from the base to the top surface and is coupled to the two side surfaces. In a preferred embodiment of this aspect of the invention, the surfaces of the housing are arranged to form a generally trapezoidal cross-section for the housing. Such a trapezoidal cross-section can increase the stability of the fluid-recovery system by lowering the center of gravity of the housing.

A second embodiment of the present invention relates to a fluid-recovery system that includes a column insert positioned within the housing for collecting a volume of the fluid from the patient, preferably the initial volume of fluid collected from the patient. The column insert can be an integral portion of the collection chamber, i.e. formed during the manufacture of the housing, or, an integral molded component of the front face, or alternatively, the column insert can be a separate structure that is positioned within the collection chamber during manufacture. The volume of the column insert is preferably selected to be less than the volume of the collection chamber to permit accurate measurement of the fluid volume within the column insert at higher resolution, i.e. in smaller volume increments.

Provision of the column insert within the collection chamber obviates the need for a cut-away portion in the collection chamber to provide a reduced volume section for collecting and measuring the initial volume of the fluid as in conventional fluid recovery systems. The presence of the column insert thus provides a separate volume for collecting and measuring the initial volume of fluid collected from the patient without substantially reducing the total volume capacity of the collection chamber. Moreover, elimination of the cut-away portion of the collection chamber increases the stability of the fluid recovery system.

According to another aspect, the column insert includes means, such as a baffle or series of baffles, for directing the initial volume of the fluid collected from the patient into the column insert. Additionally, the column insert includes overflow means, such as a notch formed within the column insert, that permits the fluid collected within the column insert to overflow from the column insert into the collection chamber once the fluid collected within the column insert substantially fills the insert.

A method for manufacturing a fluid-recovery system for collecting fluid from a patient in accordance with the present invention includes the steps of forming a housing having a base and an opening, through injection molding such that the opening defines a plane that forms an acute angle relative to the base, and attaching a face to the housing over the opening. The face is preferably attached to the housing through ultrasonic or vibrational welding.

According to one aspect of the manufacturing method of the invention, a column insert is formed, for example through a molding process, and is positioned within the housing before attaching the face to the housing.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE PREFERRED EMBODIMENTS

Figure 1:
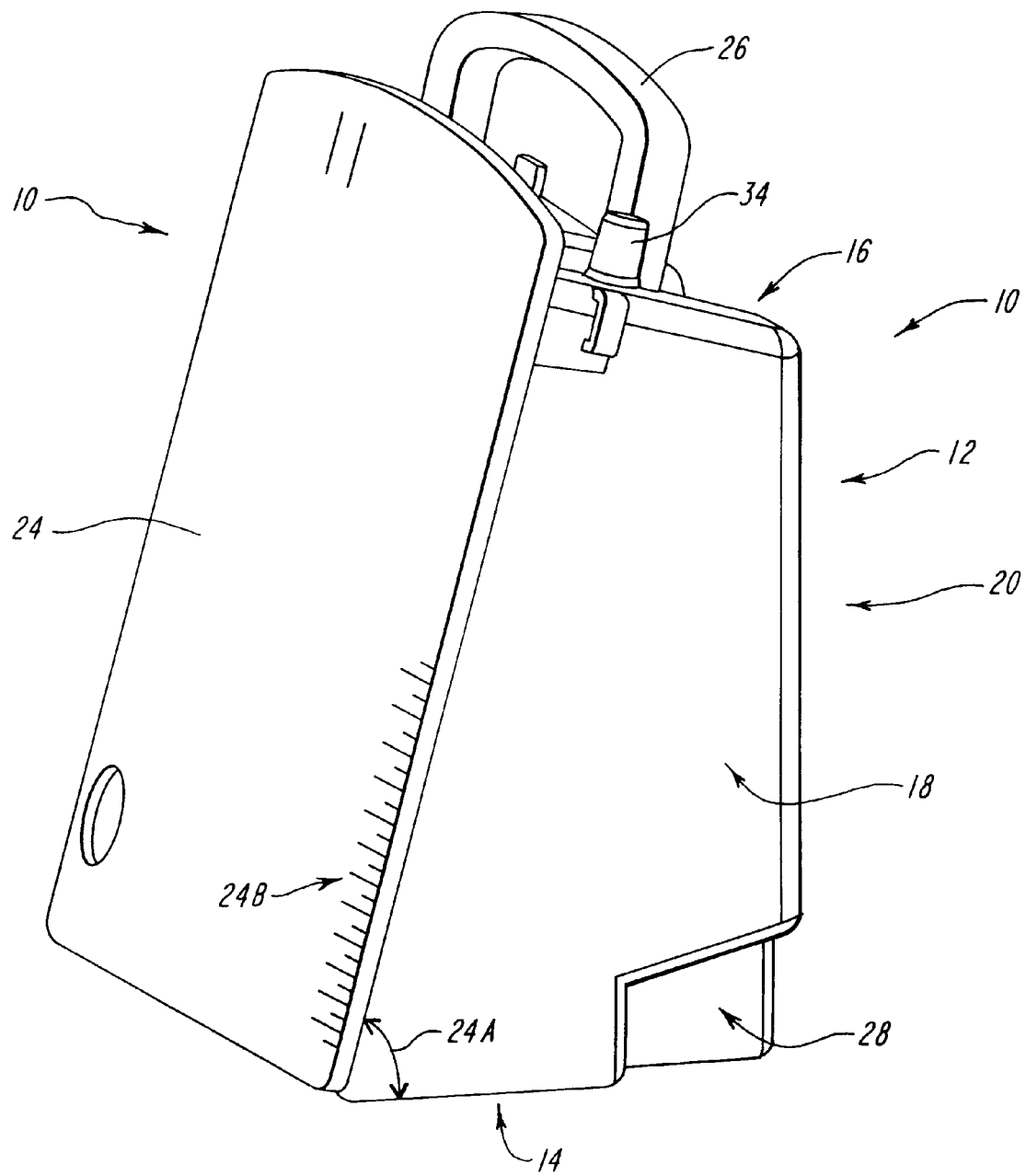
FIG. 1 is a perspective view of a fluid recovery system according to the teachings of the invention.
Figure 2:
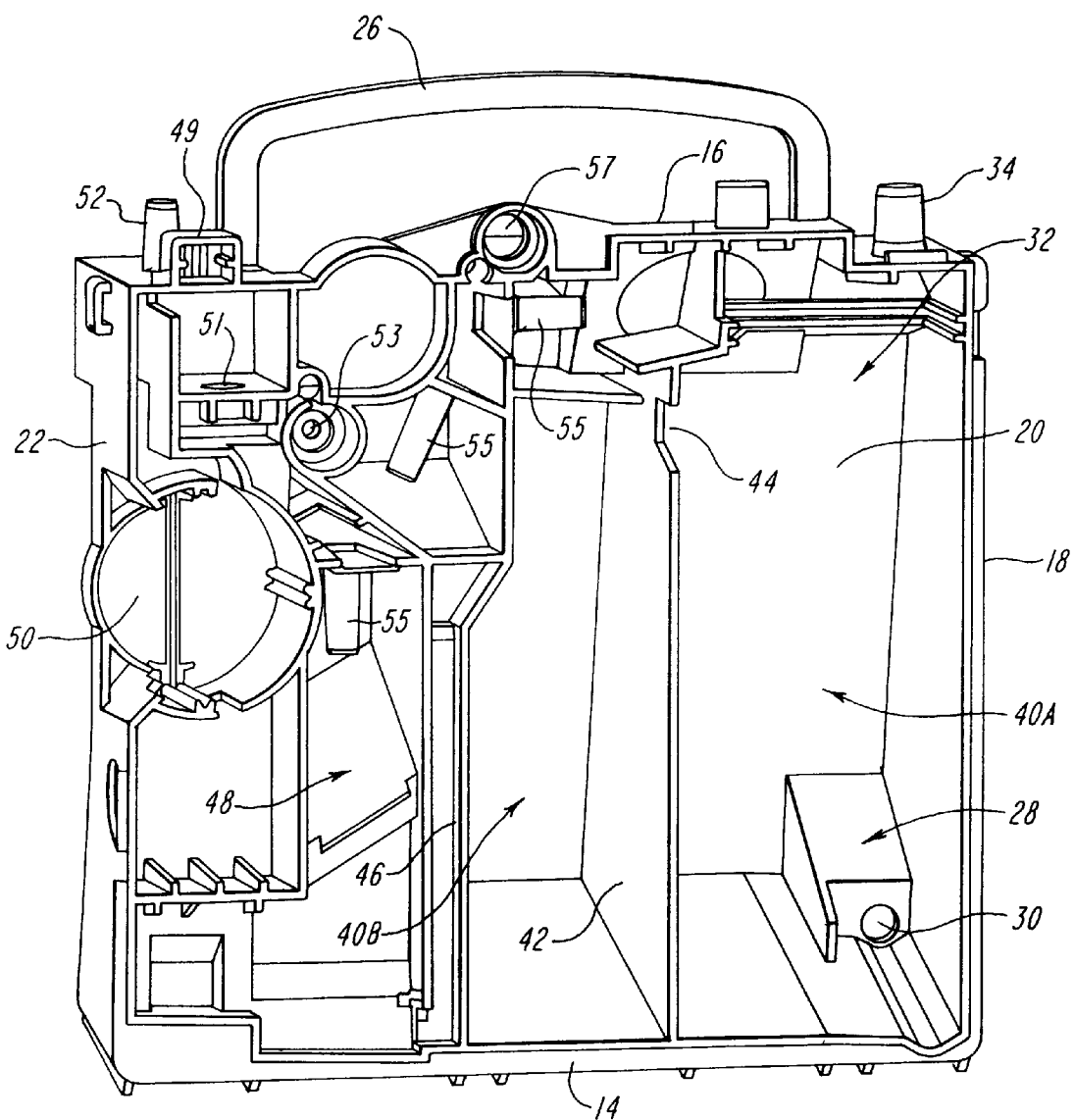
FIG. 2 is a front elevational view of the fluid recovery system of FIG. 1 with the front face removed, illustrating a collection chamber for collecting fluid from a patient.

Fluid recovery systems in accordance with the illustrative embodiments of the invention include an angled translucent front face to facilitate monitoring of the operation of the system. The illustrative fluid recovery systems can further include a column insert to measure and monitor an initial volume of fluid collected from the patient. A chest drain 10, also known as a thoracic cavity drain, according to the teachings of the invention, for draining fluids, such as blood, from the body cavity of a patient, is shown in FIGS. 1 and 2. The illustrative fluid recovery system 10 includes a housing 12 which is preferably of unitary construction, fabricated through an injection molding process. The housing 12 generally includes a base 14, a top surface 16, side surfaces 18 and 22, a rear surface 20, and a front face 24. The front face 24 extends between the base 14 and the top surface 16, and between the side surfaces 18 and 22. As discussed in more detail below, the front face 24 is positioned at an acute angle 24A to the base 14 of the housing 12. A handle 26 is secured to the housing 12 to facilitate transportation of the fluid recovery system 10. The handle 26 is preferably integrally molded to the housing 12 during the manufacture of the drain 10.

The housing 12 further includes a fluid collection chamber 32 having an inlet port 34 for receiving fluid from a patient, and directing the fluid into the collection chamber 32. A portion 24B of the front face 24 is translucent, and preferably transparent, to permit viewing the fluid collected in the collection chamber 32 and to allow monitoring of the operation of the drain 10, e.g. the magnitude of the suction force on the patient and the condition of the water seal. A graduated scale 36 having spaced markings 38, is provided on the front face 24 to permit measuring of fluid volume collected in the fluid collection chamber 32.

The spacing between successive markings of the graduated scale 36 are configured to compensate for the acute angle 24A between the front face 24 and the base 14. As the fluid is collected in the collection chamber 32, the height of the fluid, measured as the distance between the top surface of the fluid and the base 14, increases. Due to the acute angle 24A, the relationship between the change in the height of the fluid and the volume of the fluid collected is non-linear. That is, as the height of the fluid increases, a unit change in the height corresponds to less collected volume of the fluid. The graduated scale 36 is configured to compensate for this non-linear relationship between the height and the volume of the fluid collected.

A cut-away, drainage sump 28 having a fluid removal port 30 permits draining of the collected fluid from the collection chamber 32. Tubing can be attached to the fluid removal port 30 to couple flow of fluid from the collection chamber 32 to an autotransfusion pump (not shown) or transfer/infusion vessel (not shown) in situations in which autotransfusion of the collected blood is desired.

The housing 12 further is divided into a first and second fluid collection chambers 40A and 40B by an internal wall 42, as shown in FIG. 2. An overflow notch 44 formed in the internal wall 42 permits fluid communication between the first and second fluid collection chambers 40A and 40B. The second fluid collection chamber 40B receives the overflow fluid from the first fluid collection chamber 40A through the overflow notch 44 when the height of the fluid collected in the first fluid collection chamber 40A reaches the notch 44.

Figure 4:
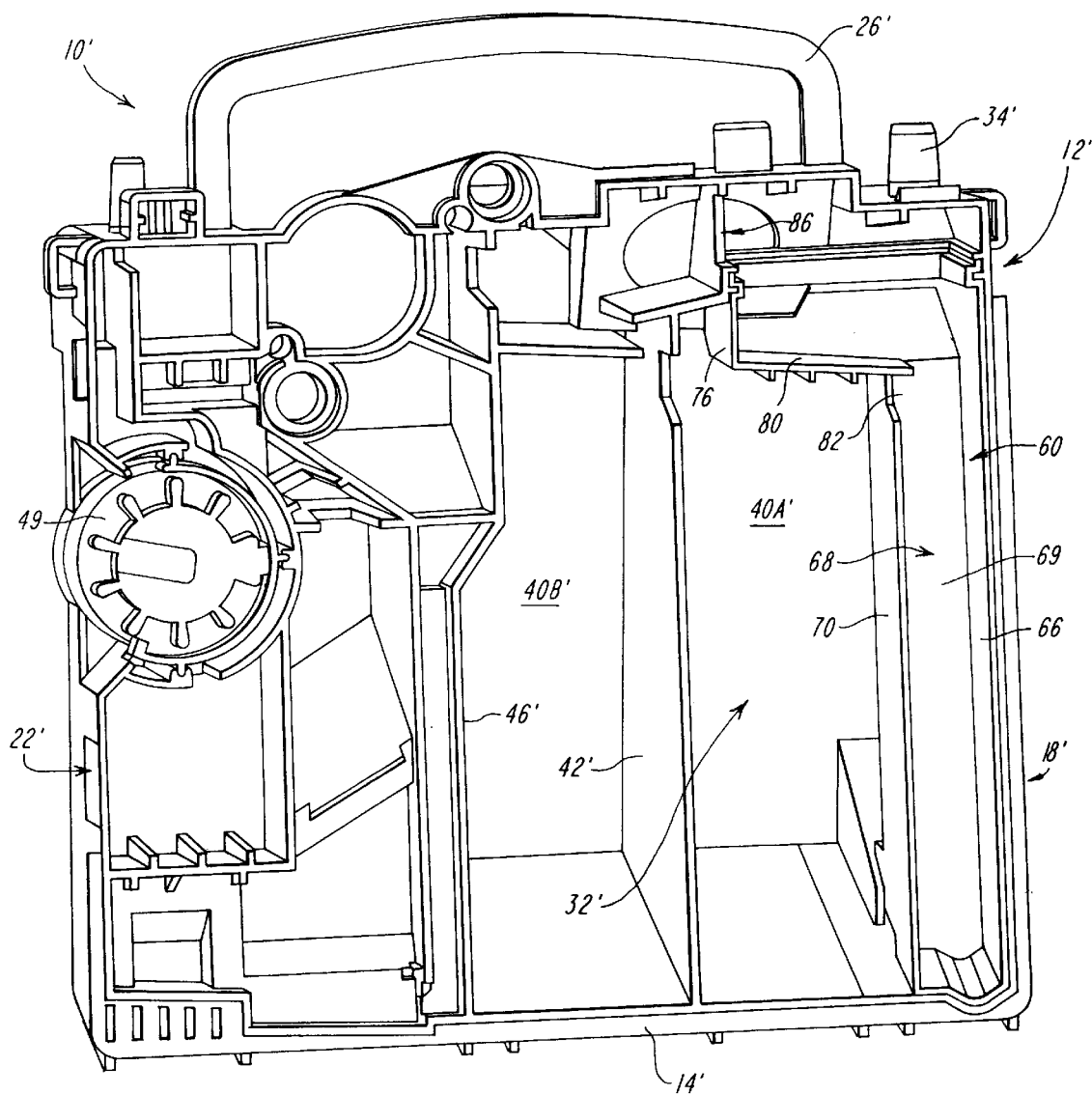
FIG. 4 is a front elevational view of second exemplary fluid recovery system in accordance with the present invention with the front face removed, illustrating a column insert positioned within the collection chamber of the fluid recovery system.

A second internal wall 46 separates the second collection chamber 40 from a water seal chamber 48 that operates as a one-way valve between a suction regulator valve 49, shown in FIG. 4, and the fluid collection chamber 32. The suction regulator valve 49 is fitted within a recess 50 and controls the amount of air entering the fluid collection chamber 32 and regulates the magnitude of suction applied to the patient. A port 52 connects the fluid recovery system 10 to a source of vacuum, such a pump or the like. The general structure and operation of the water seal chamber 48 and the suction regulator valve 49 are described in detail in U.S. Pat. No. 5,807,358, incorporated herein by reference.

Continuing to refer to FIG. 2, the water seal chamber 48 further includes a positive pressure relief valve 49, an integrally molded recess 51 for receiving a vacuum protection valve (not shown), an integrally molded recess 53 for fitting high negativity limit valve (not shown), and an integrally molded manual vent valve 57. Additionally, a plurality of knock-over nozzles 55 are provided within the water seal chamber 48 and the fluid collection chamber 32 to inhibit fluid flow, while concomitantly maintaining an open air passage, between the compartments of the water seal chamber 48 and the fluid collection chamber 32, in the event the drain 10 is knocked-over onto its front or rear surfaces 20 or 24. The structure and operation of each of these components is described in detail in U.S. Provisional Patent Application No. (Attorney Docket No. ATA-232-1), filed concurrently herewith and incorporated herein by reference.

Figure 3:
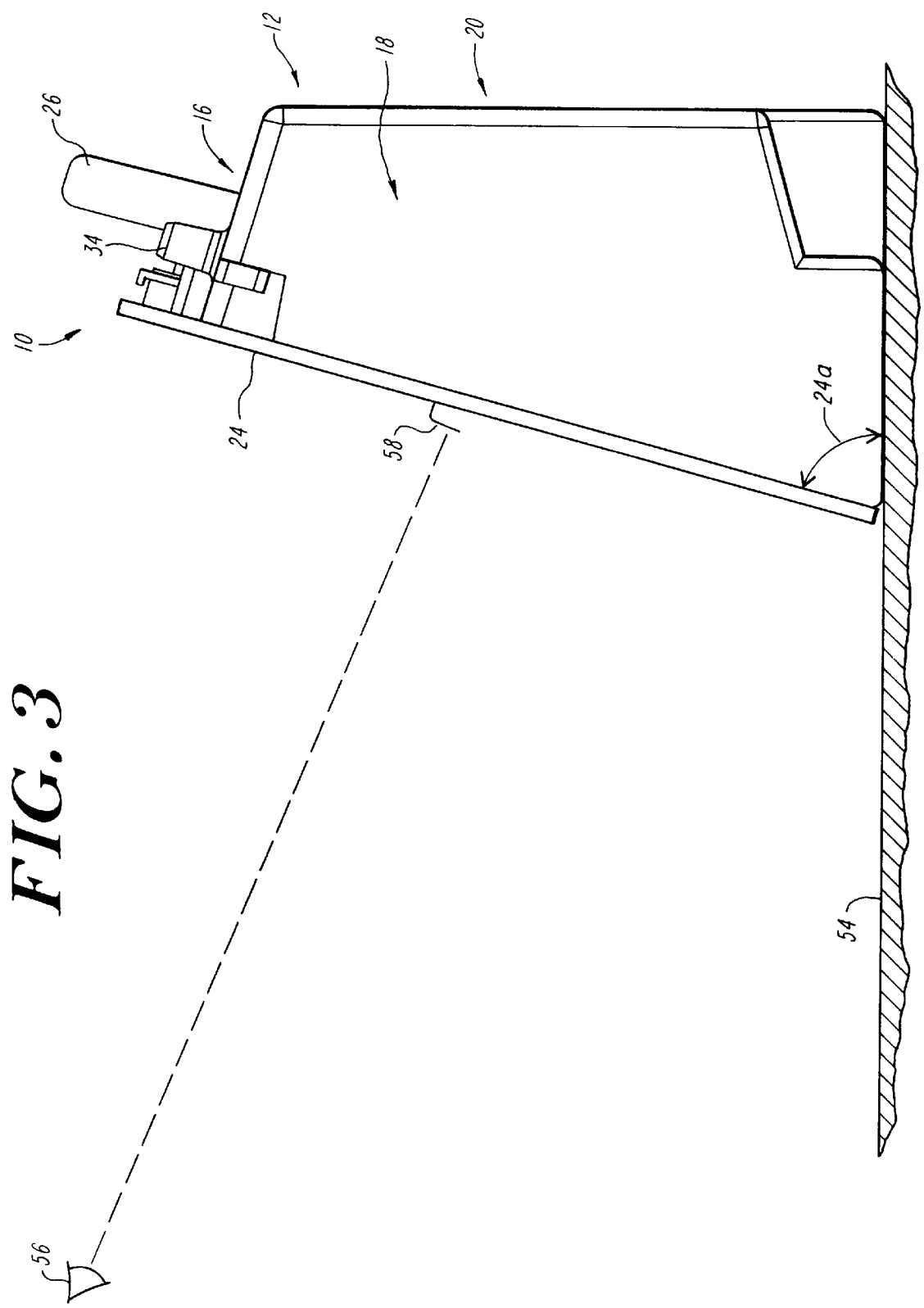
FIG. 3 is a side elevational view of the fluid recovery system of FIG. 1.

Referring to FIG. 3, the chest drain 10 is illustrated positioned on a work surface 54, such as the floor of a hospital. The acute angle 24A is selected such that a line of sight connecting the eye 56 of an observer positioned substantially above the chest drain 10, e.g. standing of the work surface 54, intersects the front face 24 of the drain 10 at a substantially perpendicular angle 58. This allows increased accuracy in determining the volume of fluid collected within the collection chamber 32 as the line of sight, in addition to being substantially perpendicular to the front face 24, is also substantially perpendicular to the markings forming the graduated scale 38, thereby facilitating reading of the markings and minimizing distortions due to the difference in height between the observer and the drain 10. Moreover, the acute angle 24A of the front face 24 can reduce the glare from overhead lights that can interfere with monitoring of the operation of the drain 10 through the translucent portion of the front face. In a preferred embodiment, the acute angle 24A is selected to be less than 85°, for example approximately 75°.

Continuing to refer to FIG. 3, the acute angle 24B of the front face 24 provides the chest drain 10 with a generally trapezoidal cross section, as formed by the front face 24, the base 14, the top surface 16, and the rear surface 20, in which the volume capacity of the drain 10 increases in the direction of the base 14. This configuration effectively lowers the center of gravity of the drain 10, thereby increasing the stability of the drain 10 and rendering the drain 10 less susceptible to knock-over. Moreover, as fluid is collected within the drain 10, the volume of fluid collected is greater proximate the base 14, further lowering the center of gravity of the drain 10 and providing further stability to the drain 10.

Figure 5:
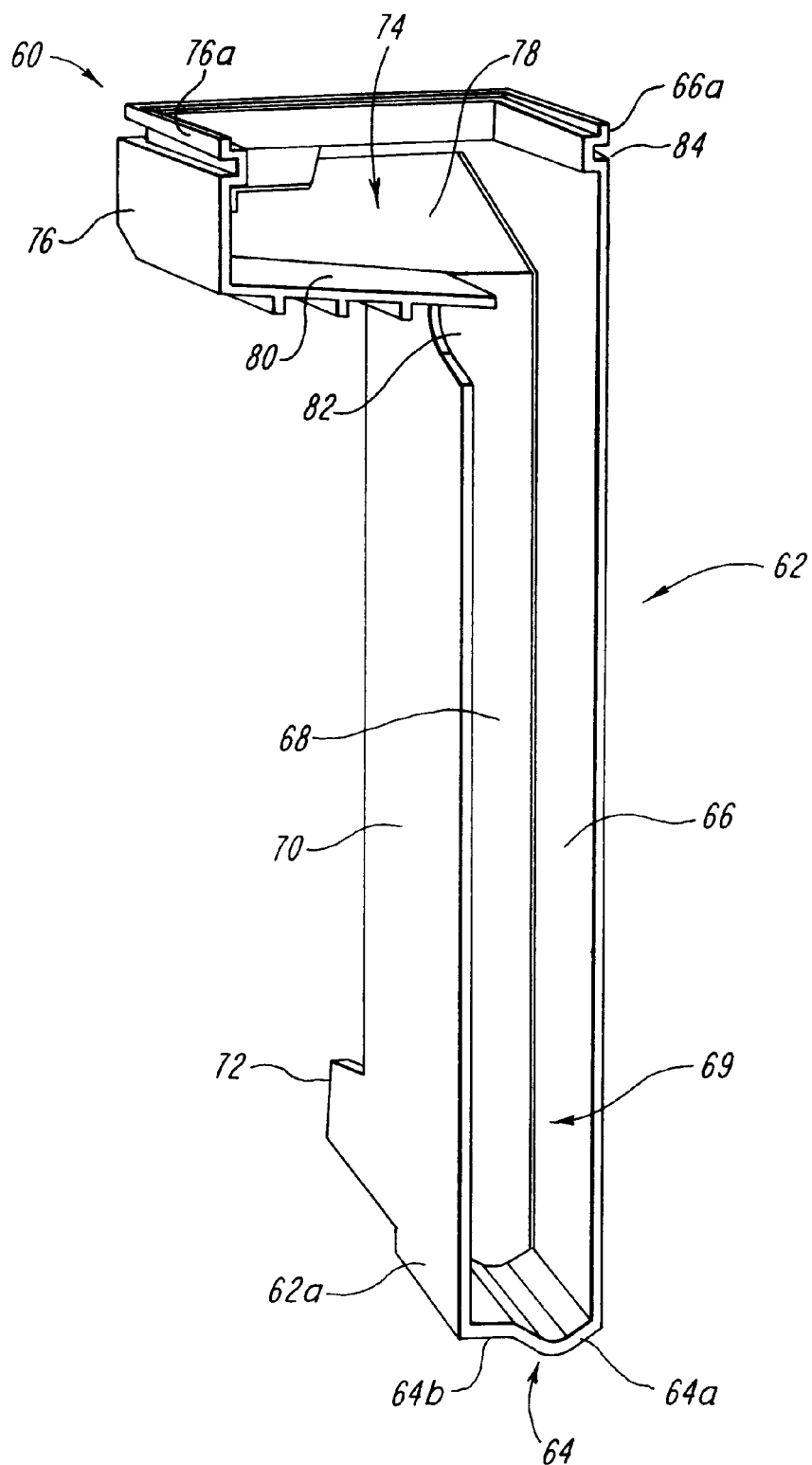
FIG. 5 is a perspective view of the column insert of FIG. 4.

Referring to FIGS. 4 and 5, a second exemplary chest drain 10' according to the teachings of the invention is illustrated. The illustrative fluid recovery system 10' includes a column insert 60 positioned within the collection chamber 32' for collecting a volume of fluid, preferably the initially collected volume of fluid, from a patient.

With specific reference to FIG. 5, the column insert 60 includes a column portion 62 formed by a base 64, and two side walls 66 and 70, and a rear wall 68, each of which is connected to the base 64. The column portion 62 includes a front opening 69 defining a plane that forms an acute angle 62A with the base 64. The acute angle 62A of the column insert 60 is preferably selected to be substantially equal to the acute angle 24A' between the base 14' and the front face 24' of the housing 12'. The front face 24' is positioned over the opening 69 and sealingly engages the side walls 66 and 70. Thus configured, the column portion 62 is a longitudinally extending tubular column having a rectangular cross section formed by the side walls 66 and 70, the rear wall 68, and the front face 24'. Alternatively, the column portion 62 can be constructed to have a circular, elliptical, or polygonal cross section.

An upper reservoir 74 formed by a portion of the side wall 66, a side wall 76, and a sloping rear wall 78, and an angled base 80 is provided above column portion 62 and functions to direct fluid from the fluid inlet 34' into the column portion 62. The rear wall 78 and angled base 80 of the reservoir 74 are angled toward the column portion 60 and operate as baffles to direct fluid into the column portion 62. A generally U-shaped slot 84 is formed in the side wall 76, the rear wall 78, and the side wall 66 along the upper portion of the reservoir 74. A gross filter (not shown) can be positioned within the column insert 60 to trap macroscopic debris such as blood clots, bone fragments, and the like entrained in the incoming fluid.

An spillover notch 82 is formed in side wall 70 immediately below the angled base 80 of the reservoir 74, i.e. at the top of the column portion 62. The overflow notch 82 permits fluid communication between the column insert 60 and the collection chamber 32. During operation of the drain 10, fluid can flow from the column portion 62 of the column insert 60 into the collection chamber 32 through the spillover notch 82 when the fluid level within the column portion 62 reaches the spillover notch 82.

The column insert 60 is preferably positioned within the first fluid collection chamber 40A' below the fluid input 34', as shown in FIG. 4. An auxiliary overflow notch 86 is formed in the upper portion of the first internal wall 42' dividing the first fluid collection chamber 40A' from the second fluid collection chamber 40B'. The auxiliary overflow notch 86 is preferably positioned on the first internal wall 42' above the column insert 60. In the event the spillover notch 82 becomes occluded with macroscopic debris, such as blood clots or bone fragments, the auxiliary overflow notch 86 allows fluid collected within the column insert 60 to flow directly into the second collection chamber

40A'. This effectively prevents fluid from backing up the patient tube into the patient, which can potentially harm the patient.

Figure 6A:
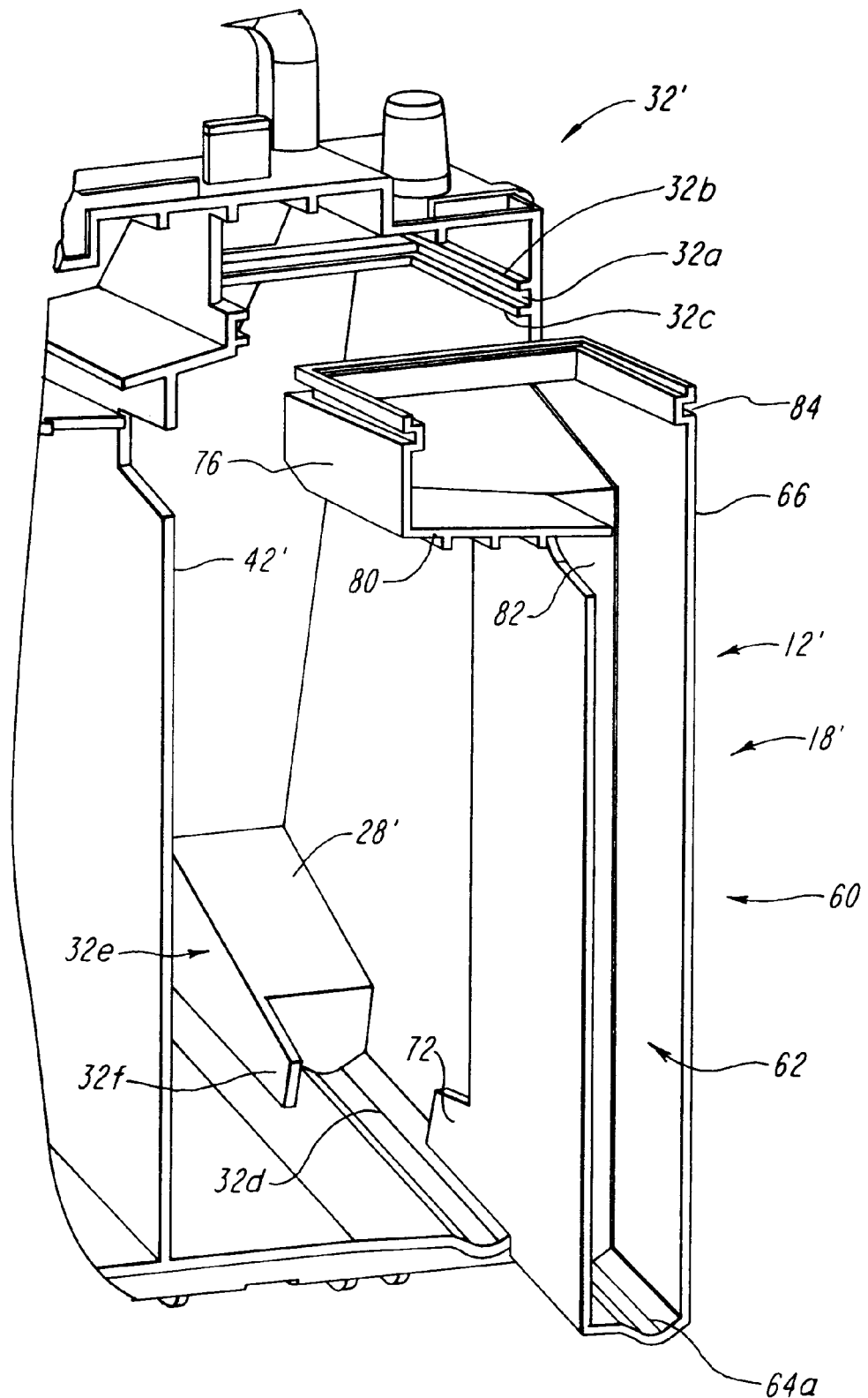
FIG. 6A is a perspective view of the column insert of FIG. 5, illustrating the installation of the column insert into the collection chamber of the fluid recovery system of FIG. 4.
Figure 6B:
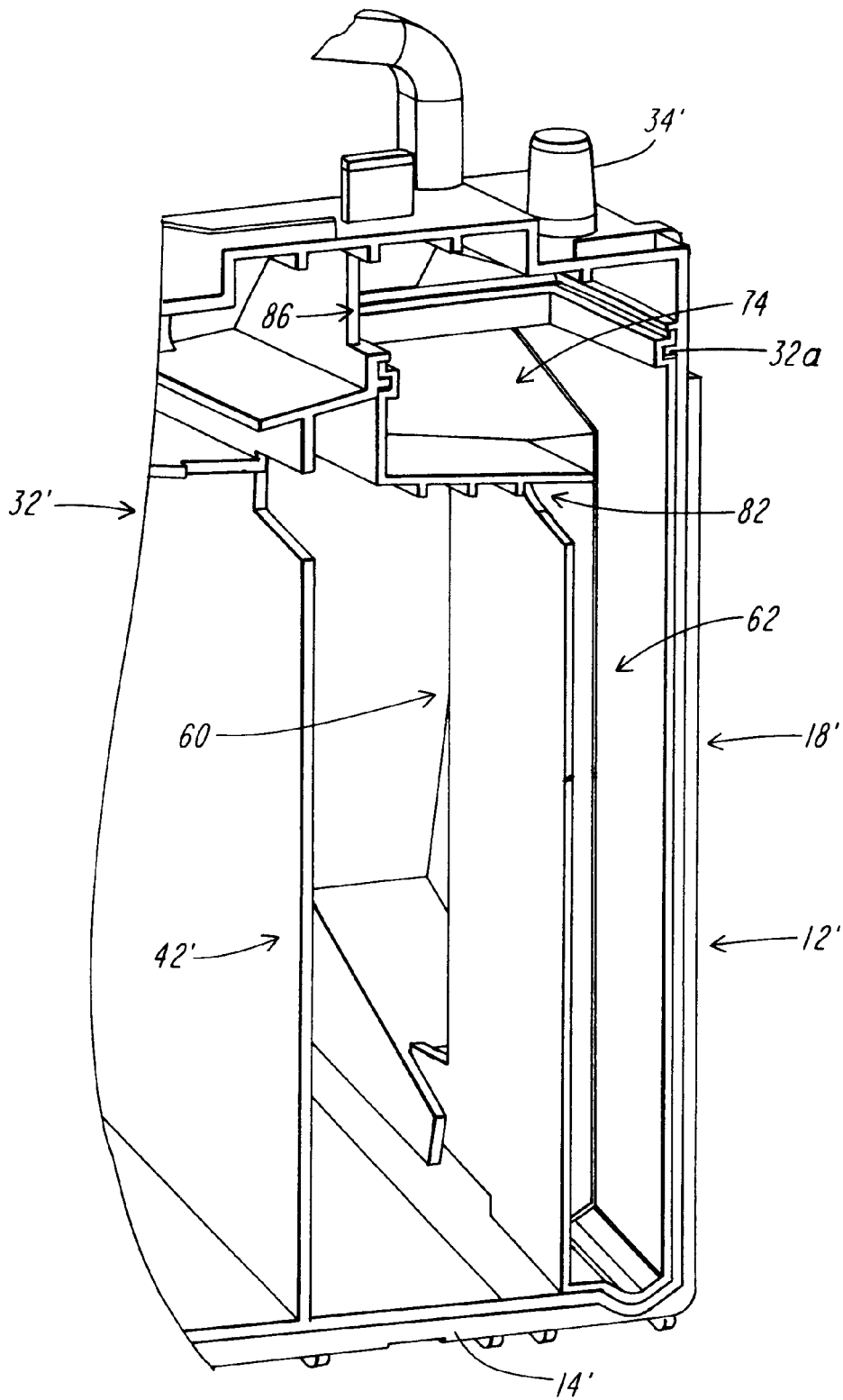
FIG. 6B is a perspective view illustrating the column insert of FIG. 5, positioned within the collection chamber of the fluid recovery system of FIG. 4.
Figure 6C:
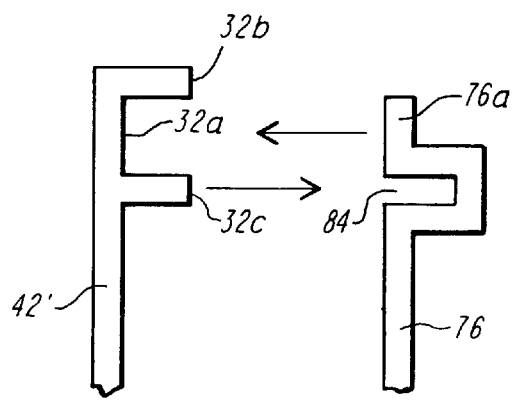
FIG. 6C is fragmentary side elevational view of a wall of the column insert of FIG. 5 and an internal wall of the collection chamber of the fluid recovery system of FIG. 4, further illustrating the installation of the column insert into the collection chamber of the fluid recovery system.

Referring to FIGS. 5, 6A, 6B, and 6C, installation of the column insert 60 into the collection chamber 32' will be described. The first fluid collection chamber 40A' includes a generally U-shaped slot 32A formed by an upper lip 32B and a lower lip 32C. The U-shaped slot 32A is sized and shaped to receive a portion, for example 76A, in FIG. 6C, of the walls 76, 78, and 66 forming the reservoir 74 of the column insert 60 above the slot 84, preferably in a friction-tight fit, as best illustrated in FIG. 6C. Additionally, the lower lip 32 is similarly received in the slot 84. One skilled in the art will appreciate that shape of the slot 32A is not limited to the shape described-above, and that other shapes may be employed and, also, that the slot 32A need not extend completely around the periphery of the chamber as illustrated.

The base 64 of the column insert 60 includes an arcuate concave portion 64A joined to a generally flat portion 64B. The base 14' of the collection chamber 32' likewise includes an arcuate concave slot 32D for receiving concave portion 64A of the base 64 of the column insert 60. The slot 32B and the concave portion 64A are preferably symmetrically concave. A rearward extending, substantially flat support 65 extends from the rear surface 68 of the column insert 60. A mating flat support 32F extends from the rear wall 32F of the section of the housing 12' forming the sump 28'.

Referring to FIG. 6B, when the column insert 60 is installed in the collection chamber 32', the upper portions 76A, 78A, and 66A of the reservoir walls 76, 78, and 66, are received within slot 32A of the housing 12'. The lower lip 32C fits within the slot 84 of the column insert 60 along the entire length of the slot 84. The concave portion 64A of the column insert 60 seats within concave portion 64A of the base 14' of the housing 12'. The side wall 66 of the column insert 60 is preferably adjacent to and in contact with the side wall 18' of the housing 12'. The flat support 72 is positioned inside of and in contact with the mating flat support 32F of the housing 12'. When completely inserted, the front opening 69 of the column insert 60 is flush with the front opening of the collection chamber 32. The front cover 24' is bonded to the housing 12' and the column insert 40, preferably by ultrasonic or ultrasonic welding.

In operation, reservoir 74 of the column insert 60 directs fluid from the patient the inlet port 34' of the drain 10' into the column portion 62 of the column insert 60. Fluid collected within the column insert 60 fills the column portion 62 and when the fluid level reaches the spillover notch 82, fluid spills over into the collection chamber 32'.

Figure 7:
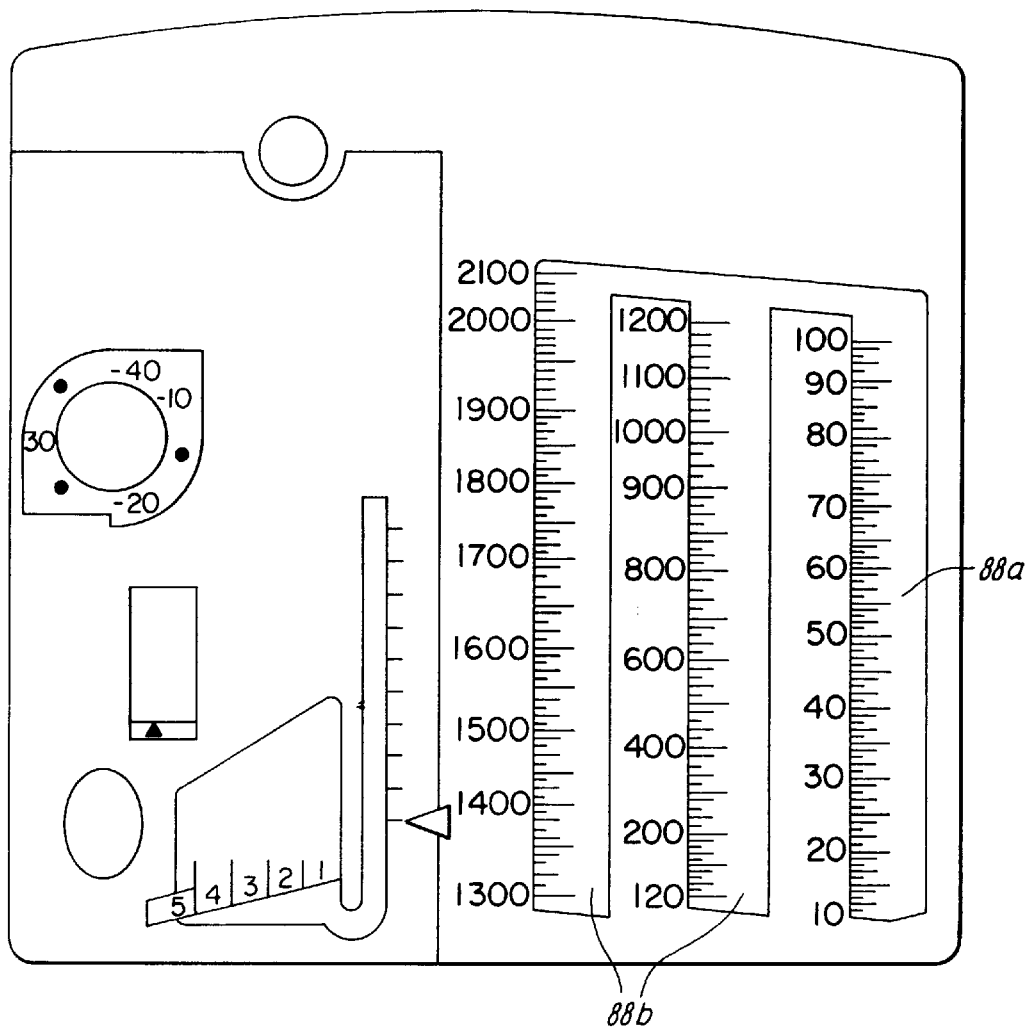
FIG. 7 is a front view of the front face of the fluid recovery system of FIG. 4, illustrating two graduated scales, a first scale having a higher resolution to indicate the volume of the fluid collected within the column insert and the second scale indicating the volume of the overflow fluid from the column insert within the collection chamber.

The column insert 60 provides a smaller volume to collect, monitor and measure fluid from the patient, compared to the first and second fluid collection chambers 40A' and 40B', without significantly reducing the overall capacity of the collection chamber 32' of the drain 10'. The smaller volume of the column insert 60 permits more accurate measurement of the fluid volume at higher resolution, i.e. at smaller volume increments. For example, referring to FIG. 7, the volume of fluid within the column insert can be accurately measured by a first graduated scale 88A in 1 cc increments, while the volume of fluid in the collection chamber 32' can be accurately measured by a second scale 88B in 10 cc increments. The smaller volume of the collection chamber 60 is accordingly particularly suited for monitoring and measuring the critical initial volume of fluid collected from the patient.

One skilled in the art will appreciate that the location of the column insert 60 within the collection chamber 32' is not limited to the arrangement described above. Nor is the column insert 60 limited in use to collecting only the initial volume of fluid from the patient. The column insert 60 can be positioned at any location within the collection chamber 32' and need not be connected to the front face 24' of the drain 10, i.e. the column insert 60 can include a front wall over front opening 69 independent of front face 24'.

Figure 8:
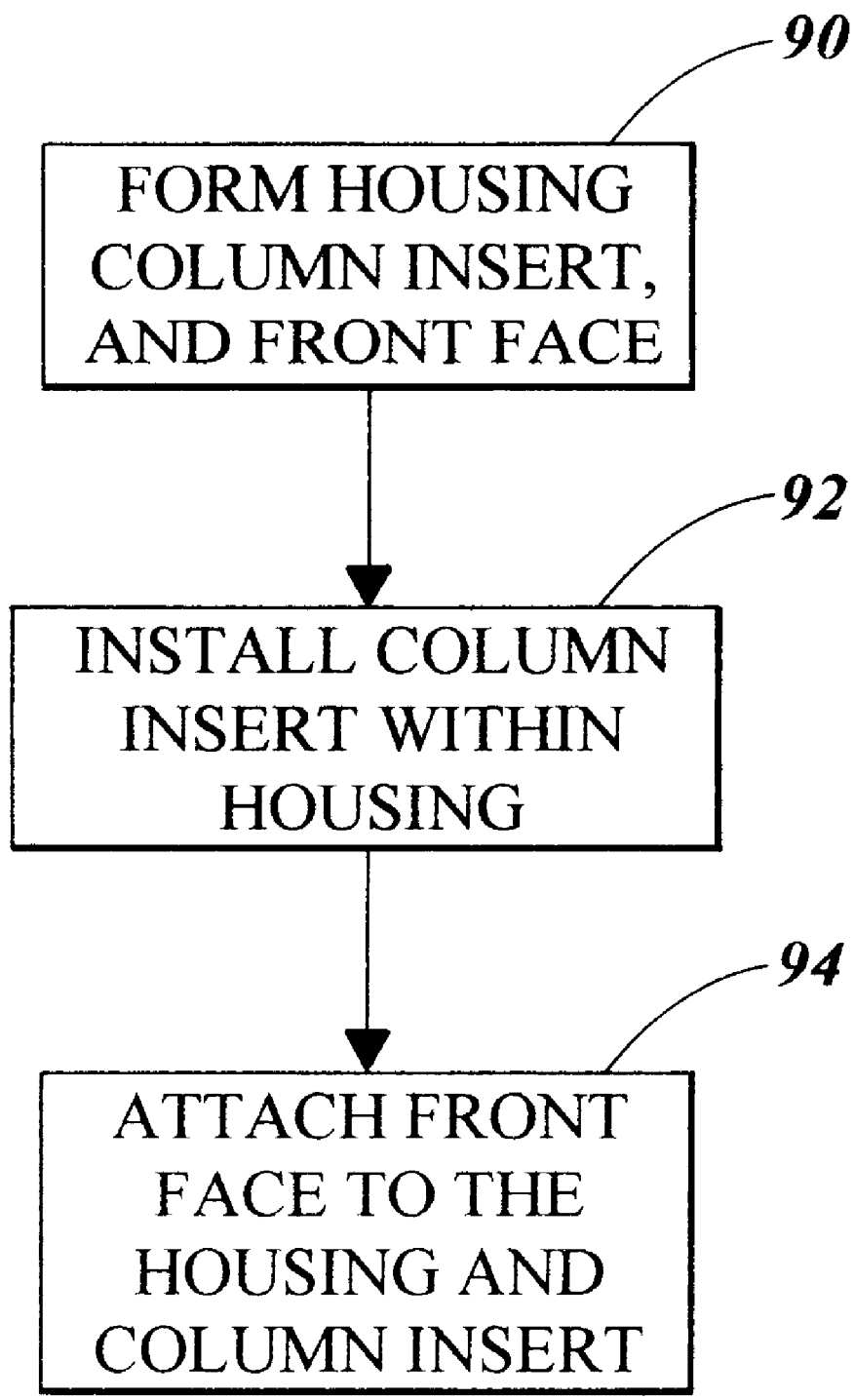
FIG. 8 is a flow chart illustrating the steps of a method for manufacturing a fluid recovery system in accordance with the teachings of the invention.

The exemplary drain 10' of the invention can be formed through an injection molding process generally illustrated in the flow-chart of FIG. 8. The housing 12', the column insert 60, and the front face 24' are preferably independently formed, through separate injection molding processes, as illustrated in block 110. In block 112, the column insert 60 is positioned within the housing 12' in the manner described above. The front face 24' is attached, preferably bonded, to the housing 12', as well as to the column insert 60, for example through ultrasonic welding, as shown in block 110, to complete construction of the drain 10'.

Those skilled in the art will appreciate that other methods can be employed to create a fluid recovery system in accord with the teachings of the invention. For example, the column insert 60 can be formed as an integral unit of the housing 12' through a molding process. Alternatively, the column insert 60 can be formed integrally to the front face 24' housing and attached with the front face 24' to the housing 12'.

Figure 9:
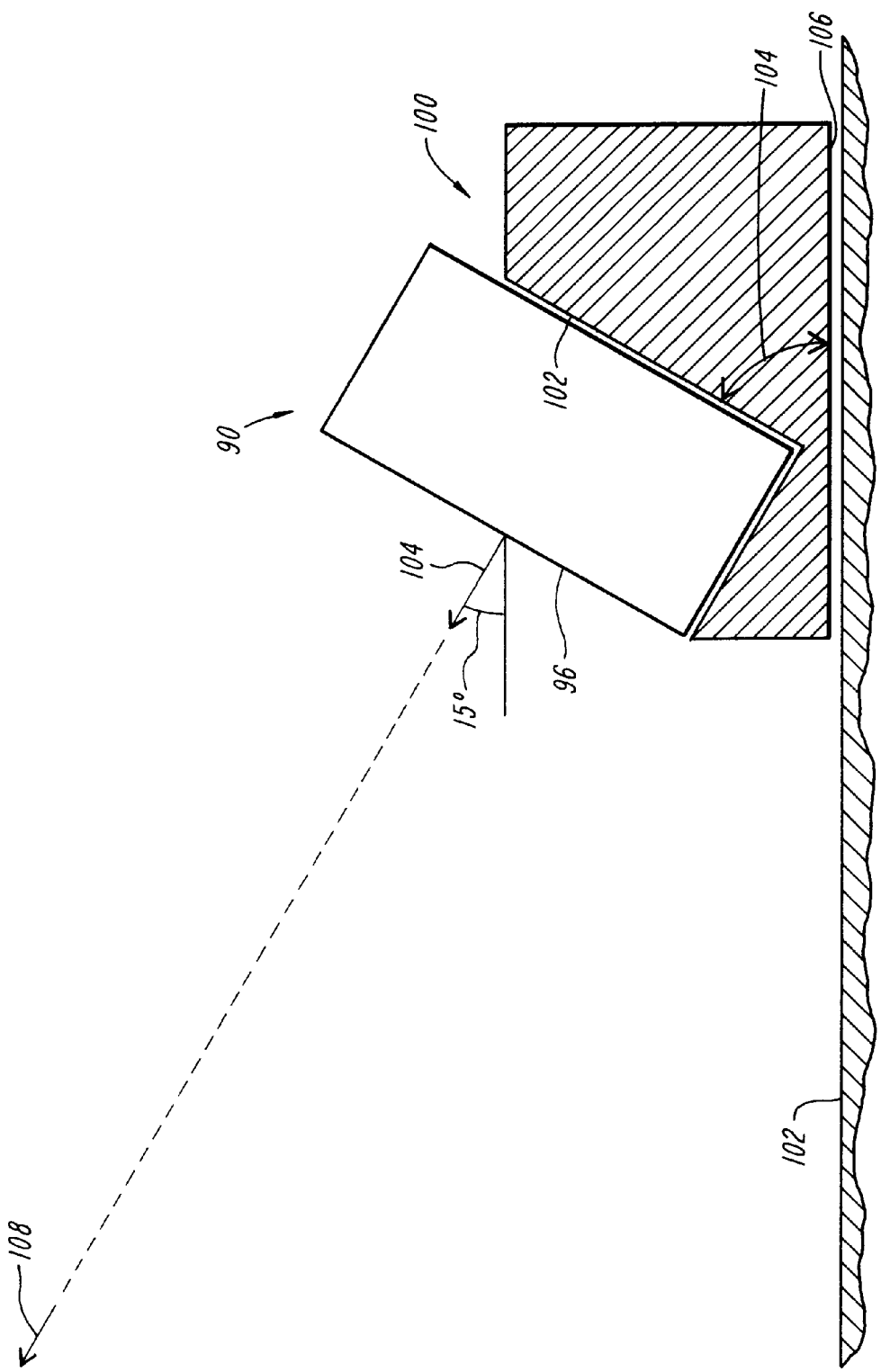
FIG. 9 is a side elevational view of stand for supporting a fluid recovery system at angle to a work surface according to the teachings of the invention.

In an alternative embodiment of the invention, a stand 100 is provided to receive a conventional rectilinear fluid recovery device, such as chest drain 90, as illustrated in FIG. 9. The stand 100 is configured to position the drain 90 such that the fluid collected within the drain 90 can be conveniently monitored and measured through the front face 96 of the drain from a position substantially above the system. A stand 100, seated on a work surface 102 such as the floor of a hospital, supports the drain 90 such that the line of sight 104 from the eye 108 of an observer viewing the front face is substantially perpendicular to the front face 96, in a manner analogous to above-described embodiments. The stand 100 can include an angled support surface 102 that is positioned at angle 104 to the base 106 of the stand 100 and the work surface 102. Preferably the angle 104 is less than or equal to 85°. The stand 100 can be made of plastic and molded to acquire the requisite shape or, alternatively, can be made of metal, such as stainless steel, or other materials suitable for use in a hospital environment.

Although the features and principles of the exemplary fluid recovery system of the invention described above have been illustrated in connection with a so-called dry chest drain employing a suction regulator valve 49, one skilled in the art will appreciate that these features and principles, e.g. the acutely angled front face and the column insert, can be used with any type of chest drain, including, for example, a so-called wet chest drain. An exemplary wet chest drain, including a manometer chamber for regulating air flow and suction to the patient, is described in detail in U.S. Pat. No. 5,397,299, incorporated herein by reference.

Likewise, the features and principles of the present invention described above, in particular the acutely angled front face and the column insert, are not limited in use to a chest drain or thoracic cavity drain, but can be used in connection with any apparatus for collecting fluid from a patient, including, for example a cardiotomy reservoir.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A fluid recovery system for collecting fluid from a patient, comprising
    a housing having a base and including a collection chamber for collecting a volume of the fluid from the patient, and
    a front face coupled to the base, at least a portion of the front face permiting viewing of the volume of fluid collected within the collection chamber, and the front face being positioned at an acute angle relative to the base to facilitate monitoring operation of the fluid recovery system through the front face.

2. The fluid-recovery system of claim 1, further comprising a graduated scale provided on the front face for measuring the volume of fluid collected, the graduated scale being configured to compensate for the angle of the front face.

3. The fluid-recovery system of claim 1, wherein the acute angle is less than or equal to 85°.

4. The fluid recovery system of claim 1, wherein the housing includes top surface, a rear surface and two side surfaces, the front face extending between the base and the top surface of the housing and being coupled to the two side surfaces.

5. The fluid recovery system of claim 4, wherein the front face, the base, the top surface, and the rear surface of the housing are arranged to provide a generally trapezoidal cross-section to the housing.

6. The fluid recovery system of claim 1, wherein the acute angle is selected such that a line of sight between a user and the front face is substantially perpendicular to the front face.

7. A fluid recovery system for collecting fluid from a patient, comprising
    a housing having a base and including a collection chamber for collecting a volume of fluid from the patient, and
    means for facilitating monitoring operation of the fluid recovery system through a translucent front face from a position substantially above the fluid recovery system, wherein the means for facilitating monitoring comprises a surface of the housing positioned at an acute angle relative to the base, at least a portion of the surface being translucent to permit viewing of the volume of fluid collected within the collection chamber.

8. The fluid recovery system of claim 7, wherein the housing includes a translucent surface permitting monitoring of operation of the fluid recovery system, and
    wherein the means for facilitating monitoring comprises a stand configured to receive the housing and position the translucent surface at an acute angle relative to a work surface.

9. The fluid-recovery of claim 7, further comprising graduated markings provided on the surface to facilitate measurement of the volume of fluid collected within the collection chamber, the graduated markings being spaced to compensate for the angle of the surface.

10. The fluid-recovery system of claim 7, wherein the acute angle is less than or equal to 85°.

* * * * *